United States Patent [19]

Chaumette et al.

[11] Patent Number: 5,786,393
[45] Date of Patent: Jul. 28, 1998

[54] LIQUID PHASE PROCESS FOR CONVERTING SYNTHESIS GAS

[75] Inventors: Patrick Chaumette, Bougival; Pierre Boucot, Ternay; Pierre Galtier, Vienne Cedex, all of France

[73] Assignee: Institut Francais du Petrole, Cedex, France

[21] Appl. No.: 679,256

[22] Filed: Jul. 12, 1996

[30] Foreign Application Priority Data

Jul. 13, 1995 [FR] France .................. 95 08637

[51] Int. Cl.⁶ .................. C07C 27/00
[52] U.S. Cl. .................. 518/700
[58] Field of Search .............. 252/373; 518/700, 518/713, 715

[56] References Cited

U.S. PATENT DOCUMENTS 4,413,063 11/1983 Audibert .
4,529,738 7/1985 Sugier et al. .

FOREIGN PATENT DOCUMENTS

| 0 188 304 | 7/1986 | European Pat. Off. . |
| 897 549 | 10/1953 | Germany . |
| 7708307 | 1/1979 | Netherlands . |
| 728543 | 4/1955 | United Kingdom . |

*Primary Examiner*—Gary Jeist
*Assistant Examiner*—Karl J. Puttlitz, Jr.
*Attorney, Agent, or Firm*—Millen, White, Zelano & Branigan, P.C.

[57] ABSTRACT

In the synthesis of essentially linear saturated $C_5^+$ hydrocarbons from synthesis gas, the reactive gas phase circulating either as a downflow or as an upflow through a fixed bed catalytic reaction zone, an upflow of an inert liquid phase through said zone at a superficial flow rate of more than 0.01 cm/s, as compared to a downflow of liquid phase, increases the selectivity of the process to the formation of the desired $C_5^+$ cut.

13 Claims, 2 Drawing Sheets

LIQUID PHASE PROCESS FOR CONVERTING SYNTHESIS GAS

FIELD OF THE INVENTION

The present invention concerns a process for the synthesis of essentially $C_5^+$ hydrocarbons (i.e., hydrocarbons containing at least 5 carbon atoms per molecule) from synthesis gas, for use as a liquid fuel or motor fuel.

BACKGROUND OF THE INVENTION

Synthesis gas is a $CO$—$(CO_2)$—$H_2$ mixture, i.e., a $CO$—$H_2$ mixture of carbon monoxide (CO) and hydrogen ($H_2$) which may also include carbon dioxide ($CO_2$). The synthesis of hydrocarbons from synthesis gas, which is generally carried out at a temperature in the range 150° C. to 350° C. and under pressure, is known as the Fischer-Tropsch synthesis. The catalysts which are usually used to transform $CO$—$(CO_2)$—$H_2$ mixtures to liquid or gaseous hydrocarbons generally comprise at least one metal from group VIII such as iron, ruthenium, cobalt or nickel.

The products prepared using the Fischer-Tropsch synthesis in the presence of such metallic catalysts have a very wide range of molecular weights. Thus only a small proportion of the products obtained fall into the category of middle distillates constituted by kerosine and gas oil fractions, the kerosine fraction(s) being constituted by a mixture of hydrocarbons with boiling points which are approximately in the range 140° C. to 300° C., and the gas oil fraction(s) being constituted by a mixture of hydrocarbons with boiling points which are approximately in the range 180° C. to 370° C. during atmospheric distillation as carried out by the skilled person on crude oil. The present application concerns the synthesis of essentially $C_5^+$ hydrocarbons from synthesis gas.

The Fischer-Tropsch synthesis reaction is highly exothermic. This means that when the process using this synthesis is carried out in the gas phase with a fixed bed catalyst, the carbon monoxide conversion must be limited to below 85% to avoid thermal instability in the catalytic bed, with the result that the unconverted synthesis gas must be separated and recycled.

A further process which has been proposed consists of carrying out the reaction in the presence of a liquid phase with the catalyst in suspension (a circulating bed reactor, also known as a slurry reactor). In such a case, conversion of CO can reach and even surpass 95%. On the other hand, the suspended catalyst which is circulated with the inert liquid must be separated from the reaction products then recycled.

A still further process which has been proposed consists of operating in the presence of a liquid phase which circulates from top to bottom, mixed with the synthesis gas, and a fixed bed catalyst. Thus United States patent U.S. Pat. No. 4,413,063 claims a process for synthesising hydrocarbons or alcohols from synthesis gas in the presence of a catalyst and an inert diluent, the synthesis gas circulating downwards mixed with the liquid phase and through the fixed bed catalyst. This trickle bed downflow reactor containing a fixed bed with liquid and gas downflow avoids the need to circulate and separate the catalyst and limits thermal instabilities.

SUMMARY OF THE INVENTION

One aim of the present invention is to provide a process which avoids the disadvantages of fixed bed/gas phase processes and circulating bed processes, and which retains the advantages of a trickle bed downflow reactor, while particularly encouraging the formation of $C_5^+$ hydrocarbons over methane formation.

The process of the present invention is a process for the synthesis of essentially linear saturated $C_5^+$ hydrocarbons from synthesis gas, the reactive gas phase circulating either as a downflow or as an upflow through a reaction zone which comprises a fixed catalyst bed, the process being characterized in that it comprises an upflow of an inert liquid phase through said zone at a superficial flow rate of more than 0.01 cm/s, preferably more than 0.1 cm/s and more preferably more than 1 cm/s. The process of the invention is also termed a trickle bed upflow process.

The superficial flow rate of the inert liquid phase is defined as the ratio between the hourly space velocity, under the temperature and pressure conditions of the reaction, and the area of the transverse cross section of the reaction zone, the zone being considered without the catalyst. The optimal superficial flow rate partially depends on the size of the catalyst particles and the physico-chemical properties of the liquid. It appears to be practically independent of the superficial flow rate of the gas.

The reaction zone comprises one or more reactors, each reactor comprising at least one fixed catalyst bed. When the reaction zone comprises several reactors, these can be in series or in parallel. In all cases, the configuration of the reaction zone would be within the capabilities of the skilled person.

The catalyst particles generally have an average diameter in the range 0.2 mm to 10 mm, preferably in the range 0.5 mm to 6 mm, more preferably in the range 1 mm to 3 mm.

The catalyst can be any type of catalyst which is suitable for synthesising hydrocarbons from synthesis gas. Examples are all iron or cobalt based catalysts, which may or may not be supported, such as those described in European patent application EP-A-0 581 619 and French patent FR-A-2 677 992.

The liquid phase does not participate in the reaction and has no deleterious effect on the latter. It is preferably a hydrocarbon cut, more preferably containing essentially 10 to 20 carbon atoms per molecule, such as a gas oil cut or a kerosine cut. If the catalyst is sensitive to sulphur, a desulphurized hydrocarbon cut is preferably used. The liquid phase is preferably partially vaporisable under the reaction conditions, so as to eliminate the heat evolved by the reaction.

In a preferred implementation of the process of the invention, the liquid phase comprises at least one partially vaporisable product, for example between 0% and 80% of a product which is at least partially vaporisable. This improves heat removal and heat transfer in the reaction zone. The term "vaporisable" means any liquid product which, under the reaction conditions, is practically completely in the form of a gas. The term "partially vaporisable product" means a product of which a portion is vaporisable, generally between 10% and 100%. In the present implementation of the process of the invention, the liquid phase preferably comprises a partially vaporisable hydrocarbon cut, for example a hydrocarbon cut comprising hydrocarbons containing 5, 6, 7, 8, 9 or 10 carbon atoms per molecule.

In a preferred implementation of the process of the invention, which may or may not be independent of the preceding implementation, the inert liquid phase is advantageously obtained by recycling a portion of a hydrocarbon fraction produced by the reaction; preferably, the fraction is the gas oil or kerosine fraction of the hydrocarbons produced by the reaction. In this case, the inert liquid phase which is initially introduced into the reaction zone is supplied from outside (as opposed to a liquid phase produced in the Fischer-Tropsch reaction zone, i.e., from the inside) then the liquid phase comprises a portion of a hydrocarbon fraction produced by the reaction which is recycled to said zone. Preferably, the fraction is the gas oil or kerosine fraction.

3

By way of indication, the density of the inert liquid phase is generally in the range 0.2 g/cm³ to 2.5 g/cm³, with a viscosity in the range 0.05 centipoises to 10 centipoises (0.05 mPa.s to 10 mPa.s) under the reaction conditions. These values are not obligatory.

The best results are obtained by means of good liquid distribution at the bottom of the reaction zone using equipment which is known to the skilled person, for example a horizontal distributing plate containing a plurality of perforations.

The process of the present invention is particularly suitable for the production of a mixture of essentially linear saturated hydrocarbons from synthesis gas, generally containing at least 80% by weight, with respect to the entirety of the hydrocarbons formed, of a cut comprising $C_5^+$ hydrocarbons, and preferably less than 10% by weight of olefins in the $C_5^+$ cut. The process of the invention can thus produce essentially paraffinic hydrocarbons, in which the fraction with the highest boiling points can be converted to middle distillates (gas oil and kerosine cuts) at high yield using a hydroconversion process such as catalytic hydroisomerisation and/or hydrocracking.

The operating conditions used in the reaction depend on the nature of the catalyst and are generally as follows.

Synthesis gas is generally converted to hydrocarbons under a total pressure in the range 0.1 MPa to 15 MPa, preferably in the range 0.5 MPa to 10 MPa, the temperature being in the range 150° C. to 350° C., preferably in the range 180° C. to 270° C.

The hourly space velocity is normally in the range 100 to 20000 volumes of synthesis gas per volume of catalyst per hour, preferably in the range 400 to 10000 volumes of synthesis gas per volume of catalyst per hour.

The $H_2$/CO molar ratio in the synthesis gas is generally in the range 0.5 to 5, preferably in the range 1.2 to 3.5.

When carrying out the process of the invention, firstly the catalyst is charged into the reaction zone and pre-reduced by contact with at least one reducing compound, for example pure hydrogen or a mixture of reducing gas such as hydrogen and/or carbon monoxide, and optionally at least one inert gas such as nitrogen, the molar ratio (reducing compound):(reducing compound+inert gas) being in the range 0.001:1 to 100:1 when at least one inert gas is present. Pre-reduction is generally carried out between 150° C. and 600° C., preferably between 200° C. and 500° C., between 0.1 MPa and 10 Mpa, and at an hourly space velocity of 100 to 40000 volumes of mixture per volume of catalyst per hour. Pre-reduction can optionally be carried out in the liquid phase, the liquid phase for pre-reduction being, for example, constituted by at least one hydrocarbon containing at least 5 carbon atoms per molecule.

BRIEF DESCRIPTION OF THE DRAWINGS

FIGS. 1 and 2 are preferred embodiments and FIG. 3 is comparative.

The following examples illustrate the invention without in any way limiting its scope.

EXAMPLES

The catalyst used in Examples 1 to 4 was prepared as follows:

75 g of a colloidal solution of silica containing 40% by weight of $SiO_2$ (Ludox 40) and 2 ml of 10% nitric acid were added gradually and simultaneously to a solution containing 40 g of cobalt nitrate (to keep the pH between 1 and 2), 1 g of hexamine ruthenium trichloride and 0.3 g of trihydrated copper nitrate dissolved in 50 ml of water. The solution was not stirred for 10 minutes, then 25 g of Ludox AS40 was added, the pH increasing and stabilising between 5.5 and 6.5. After 12 minutes, a silica gel containing cobalt, copper and ruthenium salts had formed.

The gel obtained was separated from the mother liquor by filtering, washing with water, oven drying at 40° C. to 120° C. then calcining at 450° C. and forming by pelletization. The 5×5 mm pellets were then calcined again at 600° C.

The catalyst was reduced in the reactor prior to hydrocarbon synthesis using a mixture containing 6% of hydrogen in nitrogen up to 240° C., then pure hydrogen to 500° C., at atmospheric pressure.

EXAMPLE 1 (in accordance with the invention)

Figure 1:
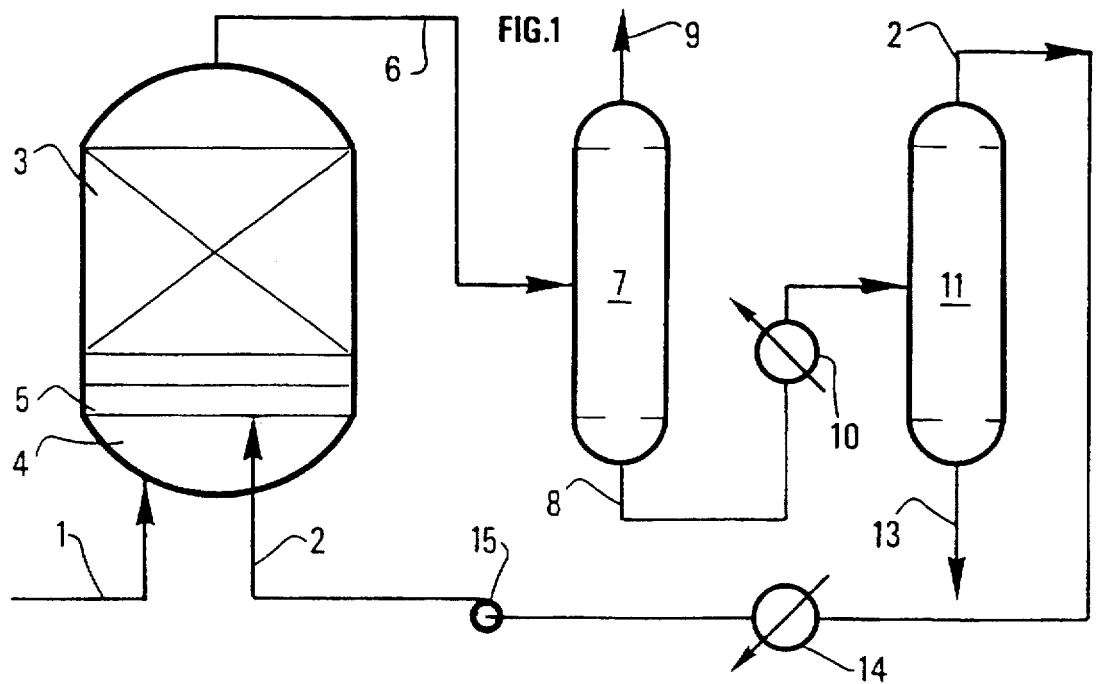
FIGS. 1, 2 and 3 are schematic flowsheets as further explained in Examples 1, 2 and 4.

In this example shown in FIG. 1, synthesis gas ($CO+H_2$ mixture, line 1) and the liquid phase (line 2) circulated from bottom to top passing through 1.2 dm³ of catalyst 3 as described above, disposed in a fixed bed in a reactor 4. The liquid was uniformly distributed through a perforated plate 5. The effluent was evacuated via line 6. The liquid paraffins were separated from the gas at the reactor outlet in a separator 7, and sent continuously via line 8 and a reheater 10 to a separator 11. The gas from separator 7 was evacuated via line 9 and analysed by chromatography. In separator 11, the heavy paraffins synthesised in reactor 4 were separated then recovered via line 13; they were analysed by chromatography. A gas phase was recovered via line 12 which gas, after passage through a condenser 14, condensed to the liquid phase which was recycled to reactor 4 via pump 15 and line 2.

The reactor was 4 cm in diameter and 1 meter high. The synthesis gas used to synthesise hydrocarbons consisted of a mixture containing 66.7% of hydrogen and 33.3% of carbon monoxide. The gas was introduced at a flow rate of 1.2 m³/h, i.e., a GHSV (gas hourly space velocity) of 1000 h$^{-1}$. The reaction was carried out at 220° C. and 2 MPa.

The liquid phase was a paraffinic $C_{10}$–$C_{16}$ cut containing no sulphur which was introduced when the unit was started up, then separated from the effluents at the reactor outlet and recycled. The flow rate of the liquid phase was about 200 l/h at the reaction temperature, i.e., a space velocity of 4.5 cm/s. The products which were lighter or heavier than the liquid phase, and the water produced with the reaction, were separated, evacuated and analysed.

If C1, C2, C3 . . . Cn is the number of molecule-grams of carbon monoxide CO and carbon dioxide $CO_2$ (if $CO_2$ is present) transformed into hydrocarbons containing 1 to n carbon atoms per molecule, the number Nc of atom-grams of carbon in the products formed during the reaction can be calculated using the following formula:

$$Nc=C1+2C2=3C3+\ldots nCn$$

Hence:

conversion is defined as the ratio between the number Nc and the number of moles of CO and $CO_2$ (if $CO_2$ is present) in the feed, the ratio being expressed as a percentage;

methane $CH_4$ selectivity is defined as the ratio between the number C1 and the number Nc, the ratio being expressed as a percentage;

$C_5^+$ selectivity is defined as the ratio between (5C5+ 6C6+. . . nCn) and Nc, the ratio being expressed as a percentage.

Under these conditions, in Example 1, conversion was 72%, methane selectivity was 8%, and $C_5^+$ hydrocarbon selectivity was 86% (see Table 1).

EXAMPLE 2 (in accordance with the invention)

The reaction was carried out under conditions which were identical to those of Example 1, with the exception that the space velocity of the liquid phase was 1 cm/s.

Under these conditions, conversion was 80%, methane selectivity was 5%, and $C_5^+$ hydrocarbon selectivity was 90% (see Table 1).

EXAMPLE 3 (in accordance with the invention)

Figure 2:
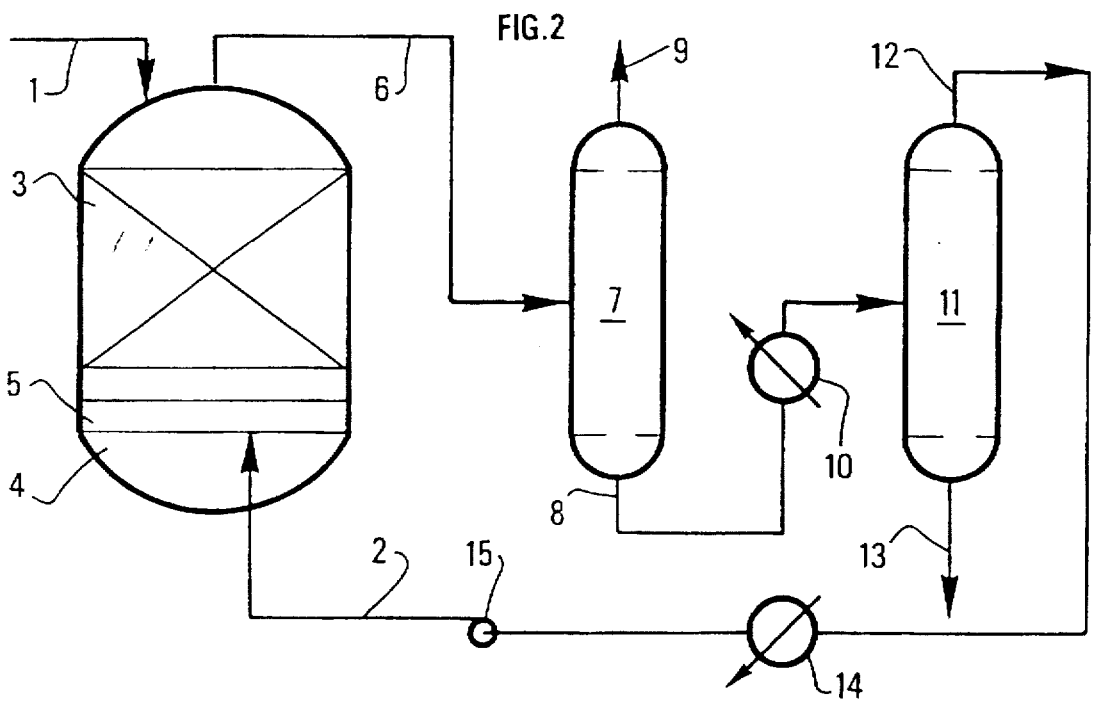

The reaction was carried out under conditions which were identical to those of Example 1, with the exception that the gas phase was circulated from top to bottom with the same HSV of 1000 h$^{-1}$. Thus in this example illustrated in FIG. 2, the synthesis gas (CO+$H_2$ mixture, line 1) circulated from top to bottom and the liquid phase (line 2) circulated from bottom to top; the two phases passed through 1.2 dm$^3$ of catalyst 3 as described above and disposed in a fixed bed in reactor 4. The other reference numerals in FIG. 2 are those of FIG. 1.

Under these conditions, conversion was 72%, methane selectivity was 6%, and $C_5^+$ hydrocarbon selectivity was 88% (see Table 1).

EXAMPLE 4 (comparative)

Figure 3:
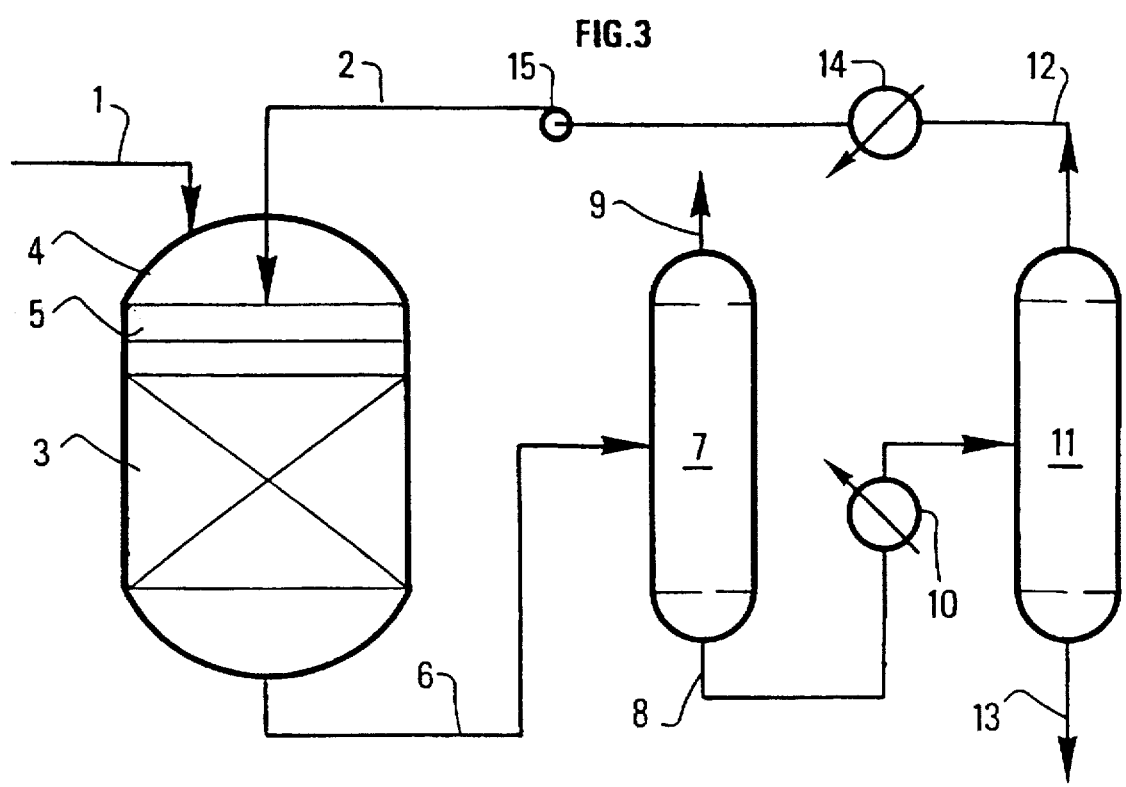

The reaction was carried out under conditions which were identical to those of Example 1, with the exception that the liquid and gas phases both circulated from top to bottom. Thus in this example illustrated in FIG. 3, the synthesis gas (CO+$H_2$ mixture, line 1) and the liquid phase (line 2) both circulated from top to bottom and passed through 1.2 dm$^3$ of catalyst 3 as described above and disposed in a fixed bed in reactor 4. The other reference numerals in FIG. 3 are those of FIG. 1.

Under these conditions, conversion was 77%, methane selectivity was 21%, and $C_5^+$ hydrocarbon selectivity was 68% (see Table 1).

TABLE 1

|  | Conversion | CH$_4$ selectivity | $C_5^+$ selectivity |
|---|---|---|---|
| Ex. 1 (upflow liquid, upflow gas) | 72% | 8% | 86% |
| Ex. 2 (upflow liquid, upflow gas) | 80% | 5% | 90% |
| Ex. 3 (upflow liquid, downflow gas) | 72% | 6% | 88% |
| Comparative Ex 4 (downflow liquid, downflow gas) | 77% | 21% | 68% |

We claim:

1. A process for the synthesis of essentially linear saturated $C_5^+$ hydrocarbons from synthesis gas, which comprises circulating a reactive synthesis gas phase either as a downflow or as an upflow through a reaction zone which comprises a fixed catalyst bed, wherein an upflow of an inert liquid hydrocarbon phase is passed through said zone at a superficial flow rate of more than 0.01 cm/s, the liquid hydrocarbon phase comprising a partially vaporizable hydrocarbon cut comprising at least one hydrocarbon with 5, 6, 7, 8, 9 or 10 carbon atoms.

2. A process according to claim 1, in which the catalyst particles have a diameter in the range 0.2 mm to 10 mm.

3. A process according to claim 2, in which said hydrocarbon cut consists essentially of containing 10 to 20 carbon atoms per molecule.

4. A process according to claim 1, in which the liquid phase is a gas oil cut or a kerosine cut.

5. A process according to claim 1, in which conversion of the synthesis gas to hydrocarbons is carried out at a total pressure in the range 0.1 MPa to 15 MPa, a temperature in the range 150° C. to 350° C., an hourly space velocity in the range 100 to 20000 volumes of synthesis gas per volume of catalyst per hour, and a $H_2/CO$ molar ratio in the synthesis gas in the range 0.5 to 5.

6. A process according to claim 1, in which the catalyst is pre-reduced in the reaction zone.

7. A process according to claim 1, in which the inert liquid phase is obtained by recycling a portion of a fraction of the $C_5^+$ hydrocarbons produced by the reaction.

8. A process according to claim 1, wherein the catalyst consists essentially of silica, cobalt, ruthenium and copper.

9. A process according to claim 5, wherein the catalyst consists essentially of silica, cobalt, ruthenium and copper.

10. A process according to claim 9, in which the liquid phase comprises at least one partially vaporisable product comprising hydrocarbons containing 5, 6, 7, 8, 9, or 10 carbon atoms per molecule.

11. A process according to claim 10, in which the inert liquid phase is obtained by recycling a portion of a fraction of the $C_5^+$ hydrocarbons produced by the reaction.

12. A process according to claim 1, wherein the process produces a product comprising 80% by weight of a $C_5^+$ cut of which less than 10% by weight constitute olefins.

13. A process according to claim 11, wherein the process produces a product comprising 80% by weight of a $C_5^+$ cut of which less than 10% by weight constitute olefins.

* * * * *